United States Patent [19]

Vaccaro

[11] Patent Number: 4,614,498
[45] Date of Patent: Sep. 30, 1986

[54] SWIVEL FOR AN ILLUMINATED DENTAL HANDPIECE

[75] Inventor: Robert K. Vaccaro, Philadelphia, Pa.

[73] Assignee: Syntex (U.S.A.) Inc., Palo Alto, Calif.

[21] Appl. No.: 702,713

[22] Filed: Feb. 19, 1985

[51] Int. Cl.⁴ ............................................... A61C 1/08
[52] U.S. Cl. ........................................ 433/126; 433/29
[58] Field of Search ............... 433/126, 105, 100, 132

[56] References Cited

U.S. PATENT DOCUMENTS

| | | | |
|---|---|---|---|
| 3,120,705 | 2/1964 | Hoffmeister et al. | 433/126 |
| 3,893,242 | 7/1975 | Lieb et al. | 433/132 |
| 3,936,940 | 2/1976 | Loge | 32/26 |
| 3,942,392 | 3/1976 | Page, Jr. et al. | 433/105 |
| 4,075,761 | 2/1978 | Behne et al. | 433/126 |
| 4,117,597 | 10/1978 | Trist et al. | 433/126 |
| 4,148,143 | 4/1979 | Fleer | 433/132 |
| 4,198,755 | 4/1980 | Landgraf et al. | 433/126 |
| 4,217,101 | 8/1980 | Loge | 433/126 |
| 4,251,212 | 2/1981 | Worschischek et al. | 433/126 |
| 4,260,382 | 4/1981 | Thomson | 433/126 |
| 4,278,428 | 7/1981 | Straihammer et al. | 433/105 |
| 4,303,392 | 12/1981 | Rollofson | 433/126 |
| 4,321,039 | 3/1982 | Schuss et al. | 433/82 |
| 4,341,518 | 7/1982 | Wallace | 433/29 |
| 4,353,697 | 10/1982 | Nakanishi | 433/29 |
| 4,354,839 | 10/1982 | Schuss | 433/126 |
| 4,398,885 | 8/1983 | Loge | 433/126 |
| 4,403,956 | 9/1983 | Nakanishi | 433/126 |
| 4,403,958 | 9/1983 | Löhn | 433/100 |
| 4,403,959 | 9/1983 | Hatakeyama | 433/126 |
| 4,431,412 | 2/1984 | Lares et al. | 433/29 |

*Primary Examiner*—Robert Peshock
*Attorney, Agent, or Firm*—Derek P. Freyberg; John A. Dhuey

[57] ABSTRACT

A swivel connector for an illuminated dental handpiece, such as a high speed or low speed handpiece or scaler, etc., permits easy rotatability and disconnectability and has good light transmission, due to the gap in the light path at the swivel being filled with water, and the use of a "nested" spring clip and bearing race minimizing friction and size.

13 Claims, 7 Drawing Figures

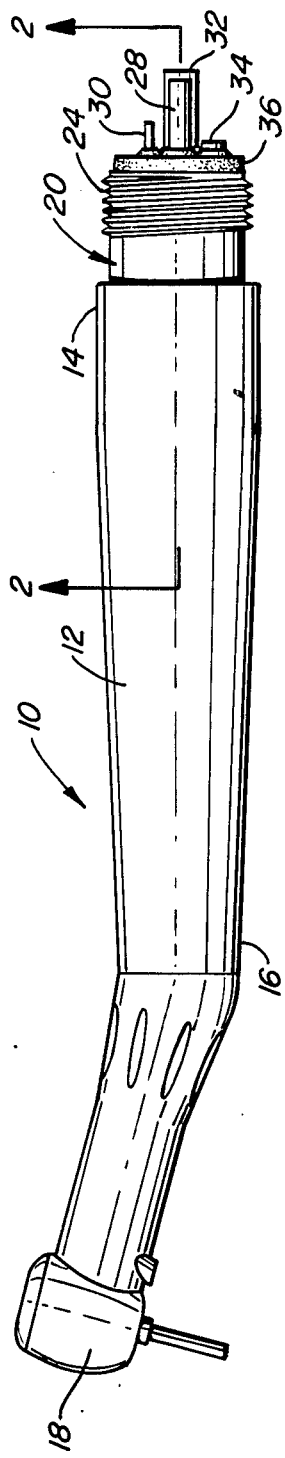
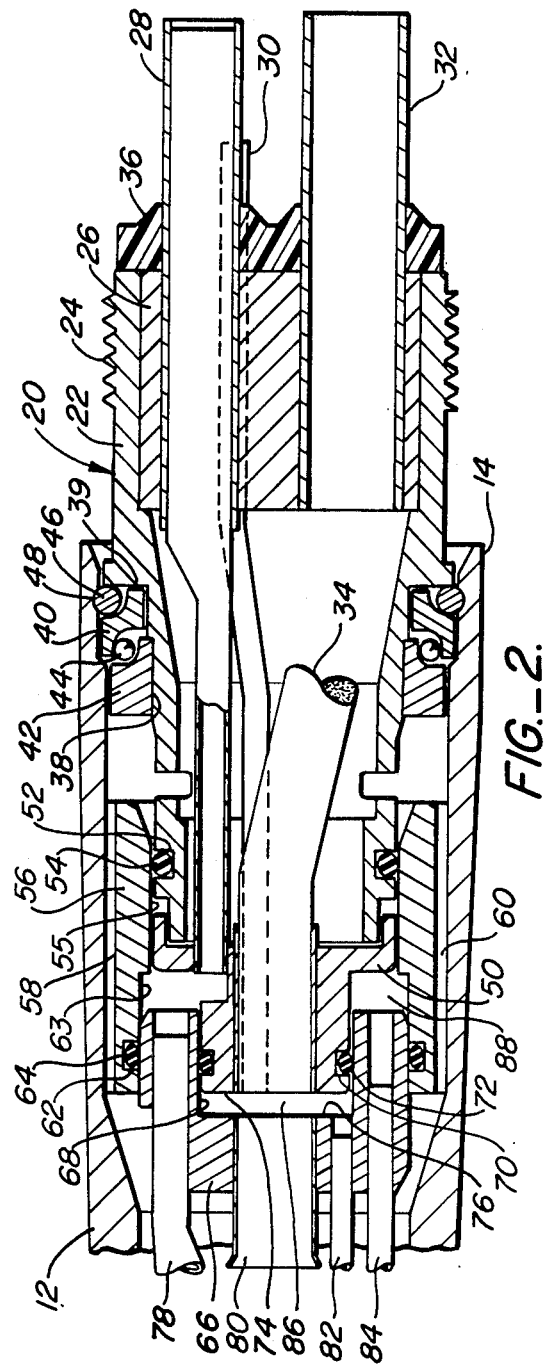

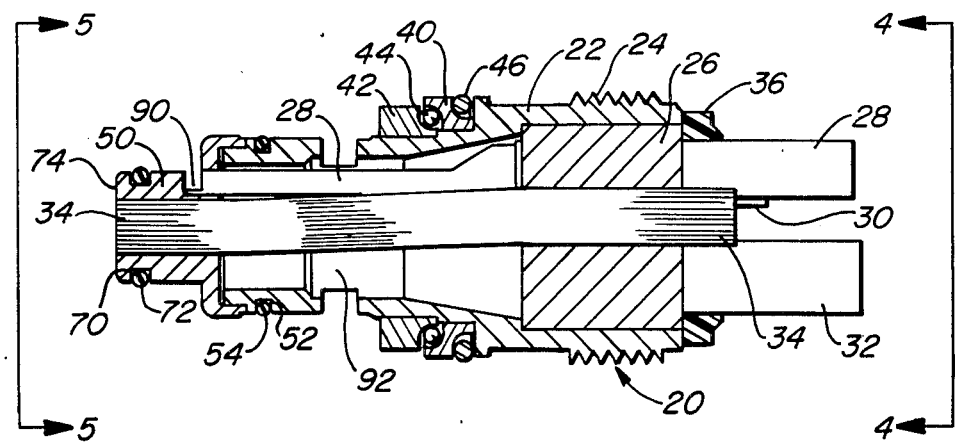
FIG._3.
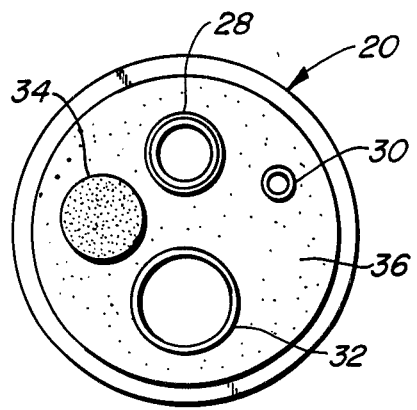
FIG._4.
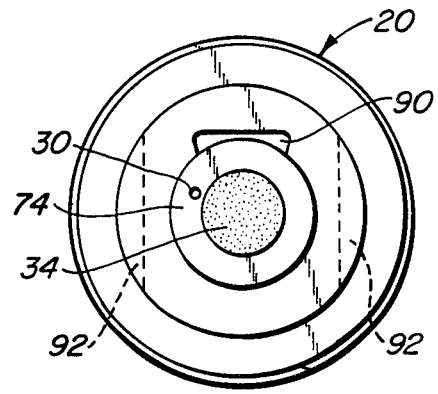
FIG._5.

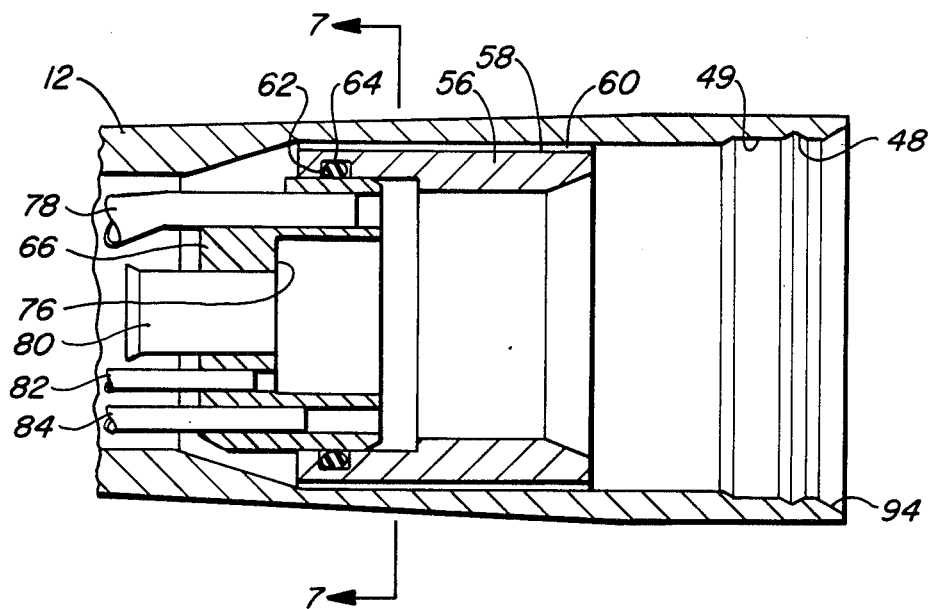
FIG._6.
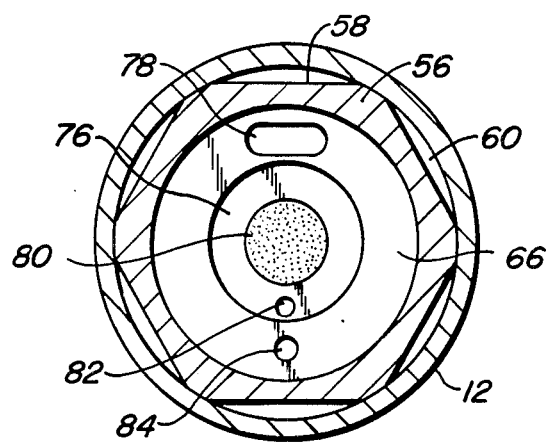
FIG._7.

SWIVEL FOR AN ILLUMINATED DENTAL HANDPIECE

BACKGROUND OF THE INVENTION

1. Field of the Invention

This invention relates to dental handpieces, and more particularly to a swivel for an illuminated dental handpiece which enables the efficient passage of light, air, and water through an easily disconnectable, rotatable connection.

2. Background to the Invention

It has been customary now for some years to provide dental handtools, especially handpieces, with a means of illuminating the operative site. The light is usually transmitted either from a bulb located in the proximal end of the tool (as used in this specification, the term "distal" refers to that end which is closest to the operative site in use, and "proximal" refers to that end remote from the operative site) or from a separate light source unit and then conveyed to the distal end via an optical fiber bundle passing through the handpiece. An example of such an illuminated handpiece is given in Wallace, U.S. Pat. No. 4,341,518.

It has also become popular to provide dental handpieces with a swivel or rotatable connection, so that that part of the handpiece near the distal end and including the part which is held by the operator may freely rotate with respect to the proximal part which is connected to the supply of operating media, such as air, water, light, and/or electric power. The rotatable connection is also preferably easily removable, so that different handpieces may be readily interchanged on the same supply (the term "handpieces" as used in this specification is intended to encompass powered drills (both high- and low-speed), powered scalers, powered endodontic instruments, and the like). Examples of handpieces including such swivels are given in, e.g., U.S. Pat. Nos. 3,936,940 and 4,217,101 to Loge; U.S. Pat No. 4,260,382 to Thomson; U.S. Pat. No. 4,303,392 to Rollofson; and U.S. Pat No. 4,321,039 to Schuss et al.

When it is desired to provide both illumination and a rotatable connection, it is generally considered desirable to route the light path along the central, longitudinal axis of the swivel connectors, at least at the point where the connection occurs, to ensure that the intensity of illumination is unaffected by the rotation. Handpieces illustrating such a light path are described in, e.g., U.S. Pat. Nos. 4,353,697 and 4,403,956 to Nakanishi; U.S. Pat. No. 4,398,885 to Loge et al.; and U.S. Pat. No. 4,431,412 to Lares et al.

Several disadvantages have been found in such handpieces. Because of the plurality of paths for operating media (typically drive air, chip or coolant air, water, light, and exhaust air), the swivel section tends to be longer and/or larger in diameter than is desirable, bearing in mind the balance and "feel" of the handpiece. Additionally, rotation tends to require a high torque because of the number of seals and other frictional contacts between rotating parts, and as the number and length of gaps in the optical path increases, a lower intensity of illumination at the operative site results. Furthermore, such swivels often tend to be complex and expensive.

It would, therefore, be desirable to provide a swivel connector for an illuminated dental handpiece which would overcome one or more of the disadvantages set forth above, and be both inexpensive and easy to use.

DESCRIPTION OF THE INVENTION

SUMMARY OF THE INVENTION

The present invention is directed to a dental handpiece comprising a housing having a distal end and a proximal end; first light conducting means within the housing to conduct light from substantially the proximal end to the distal end of the housing, the first light conducting means having a first terminus adjacent the proximal end of the housing; first liquid conducting means within the housing to conduct liquid from substantially the proximal end to the distal end of the housing; a connector having a distal end and a proximal end and being adapted for rotational attachment to the proximal end of the housing; second light conducting means within the connector to conduct light from the proximal end to the distal end of the connector, the second light conducting means having a second terminus adjacent the distal end of the connector; second liquid conducting means within the connector to conduct liquid from the proximal end to the distal end of the connector; and a manifold within the housing for sealingly engaging a portion of the connector and the first light conducting means and the first liquid conducting means, the manifold and the distal end of the connector defining a sealed space through which liquid can flow from the second liquid conducting means to the first liquid conducting means and through which light can be transmitted from the second terminus of the second light conducting means to the first terminus of the first light conducting means. In a particular aspect of the invention, the first terminus and the second terminus of the first and second light conducting means, respectively, are located on the central axis of the housing and the connector and are positioned in an opposed relationship. The handpiece can additionally include an air pathway and sealing means for substantially sealing the air pathway from leakage. The sealing means can include a seal which is responsive to the pressure in the air pathway and is sealed thereby. In still another aspect of the invention, the connector includes retaining means for engaging a cooperative portion of the housing to retain the connector within the housing while still permitting rotation of the connector. The retaining means can include a spring clip and a groove on the inside of the circumference of the housing. Rotation of the connector is facilitated by the inclusion of a bearing between the housing and the connector. In a preferred embodiment, the spring clip and the bearing are nested, and the bearing is configured to create an angular contact ball bearing.

BRIEF DESCRIPTION OF THE DRAWINGS

FIG. 1 is a perspective view of an air driven dental handpiece in which the present invention can be effectively utilized;

FIG. 2 is a cross-sectional view of a portion of the handpiece along line 2—2 of FIG. 1 illustrating the positioning of the swivel connector with respect to the housing of the handpiece;

FIG. 3 is a cross-sectional view of the connector of the present invention;

FIG. 4 is a view taken along line 4—4 of FIG. 3 illustrating one end of the swivel connector;

FIG. 5 is an end view along line 5—5 of FIG. 3 illustrating the other end of the swivel connector;

FIG. 6 is a cross sectional view of the proximal end of the housing of the handpiece; and FIG. 7 is a view along line 7—7 of FIG. 6 of that portion of the housing which connects to the swivel connector of the present invention.

DETAILED DESCRIPTION OF THE INVENTION

As illustrated with respect to the drawings, the present invention is directed to a dental handpiece 10. Typically, dental handpiece 10 is air driven. However, the swivel connector of the present invention contemplates utility in mechanically driven handpieces as well. As illustrated in FIG. 1, handpiece 10 consists generally of a housing 12 having a proximal end 14 and a distal end 16. Housing 12 is connected to an operative end 18 of handpiece 10, the operative end typically containing an air driven high speed turbine which operates a dental burr. Connected within housing 12 at the proximal end 14 is a swivel connector 20 which will be described below with more particularity.

As can best be seen from FIGS. 2, 3, 4 and 5, swivel connector 20 has a body portion 22 having a threaded proximal end 24. Retained within threaded end 24 is a bushing 26 which is adapted to receive a drive air tube 28, a water cooling tube 30, an exhaust air tube 32 and a light conductor 34. A rubber gasket 36 is fit about the foregoing tubes and conductor and facilitates connection of the handpiece to conventional delivery systems including those having ISO (International Standards Organization) connections. As can be seen in FIG. 2, the ISO connection has the light conductor 34 off-set from the center, longitudinal axis. The light conductor 34 can be bent to position the end at the distal end of connector 20 on the central, longitudinal axis. In this regard, it has been found beneficial to employ "image conduit," i.e. a collection of optical fibers which are drawn and fused together. Such a conduit can be easily heated and bent to the desired configuration. Connector 20 is formed with a diameter 38 which is adapted to support an angular contact bearing assembly consisting of an outer race 40, and inner race 42 and ball bearings 44. Additionally, outer race 40 is configured to retain a spring clip 46 between shoulder 39 and the end surface of outer race 40. When connector 20 is inserted within housing 12, Spring clip 46 is retained in a circumferential groove 48, e.g. a V-groove, formed on the inner surface of housing 12 to prevent axial movement between housing 12 and connector 20. However, connector 20 is freely rotatable within housing 12. The outer race 40 bears against a shoulder 49 also on the inner surface of housing 12.

Moving in the direction of the distal end 50 of connector 20, a groove 52 is formed to receive an O-ring 54 which is adapted to contact the inner surface 55 of an exhaust sleeve 56 in the housing 12. Exhaust sleeve 56 is formed with a hexagonal outer circumference, thus producing a series of flats 58 on the outer surface of exhaust sleeve 56 and creating spaces 60 between flats 58 and the inner wall of housing 12. A groove 62 is formed on the inner surface 63 of exhaust sleeve 56 to receive an O-ring 54 which is adapted to contact the outer surface of a manifold 66.

Manifold 66 is formed with an inner wall 68 which is sealed to the distal end of connector 20 by means of a groove 70 and an O-ring 72. Connector 20 is formed with an end wall 74 which opposes end wall 76 of manifold 66. Manifold 66 accomodates an outlet drive air conductor 78, an outlet light conductor 80, an outlet water conductor 82 and an outlet coolant air conductor 84. Additionally, the inner wall 68 of manifold 66, the end wall 74 of connector 20 and the end wall 76 of manifold 66 define a space 86 which is filled with liquid coolant as it flows from inlet tube 30 through the space 86 and out from outlet tube 82.

The configuration of exhaust sleeve 56 and connector 20 forms an air gap 88 which is annular and conveys air from inlet tube 28 through gap 88 and out of drive air tube 78 and coolant air tube 84. Exhaust air from the handpiece flows through spaces 60 toward the proximal end of housing 12 through exhaust air slots 92 formed in connector 20. The exhaust air then exits via outlet tube 32.

Connector 20 is freely rotatable within housing 12 and is axially retained therein by means of the spring clip 46 and groove 48. Spring clip 46 and retaining groove 48 constitute a quick disconnect system in the handpiece of the present invention. As connector 20 is pressed into the proximal end of housing 12, spring clip 46 is compressed radially by a conical ramp 94, seen most clearly in FIG. 6. As connector 20 is pushed further toward the distal end of housing 12, spring 48 is fully compressed and then released partially into locating groove 48. Nesting of spring clip 46 and ball bearings 44 upon outer race 40 of the bearing assembly results in substantial space savings in that spring clip 46 and ball bearings 44 occupy substantially the same radial space. Inner race 42 is pressed on to body 22 of swivel connetor 20 such that when connector 20 is being pulled outwardly from the proximal end of housing 12, inner race 42 presses on balls 44 forcing outer race 40 against spring clip 46 thus compressing the spring and facilitating removal. The angular contact bearing assembly provided by inner race 42, ball bearings 44 and outer race 40 additionally facilitates free rotation of connector 20 within housing 12 since angular contact bearing assemblies take axial load as well as radial load without binding during rotation.

In order to additionally reduce the frictional forces involved in the rotational elements of the present invention, a so called "floating O-ring" 54 is provided in groove 52. O-ring 54 is dimensioned such that its inside diameter is larger than the inner diameter of groove 52 to provide some looseness of fit and thus create a low friction surface. O-ring 54 is sealed at its outer circumference by contacting the inner wall 55 of exhaust sleeve 56 and the edge of groove 52 which can be seen most clearly in FIG. 2. The pressure of the drive air forces O-ring 52 against the contact surfaces and while some leakage can be tolerated and typically is present, the low pressure provides contact surfaces having substantially low co-efficient of friction thus facilitating free rotation of connector 20 within housing 12.

In order to provide smooth operation of a turbine assembly in a typical hand driven handpiece, air slot 90 in connector 20 is provided in the top surface of a portion of body 22 of connector 20 in a recessed fashion to provide a baffling action for the drive air being transmitted to outlet tube 78. The baffling effect reduces variations in the pressure supplied to outlet tube 78 and subsequently to the air driven turbine and facilitates smooth operation of the handpiece.

An additional and substantial aspect of the present invention is the use of water in the space or gap 86 between the ends of light conductors 34 and 80. When light travels from air into glass or glass into air, most of the light is transmitted while some is reflected back and lost. Additionally, light leaving an optical glass fiber exits in a diverging cone. The angle of divergence is determined by the angle of incidence at the beginning of the fiber as well as the refractive indices of the core glass and the adjacent medium. In order to minimize the reflective losses and the losses due to divergence across the light gap, the gap is filled with water, which has an index of refraction closer to the index of refraction of glass. The amount of light which is reflected can be approximately determined by the equation $R = ([n_1 - n_0]/[n_1 + n_0])^2$ wherein R = the Fresnel reflection co-efficient, $n_0$ = the index of refraction of the adjacent medium and $n_1$ = the index of refraction of the glass. For a typical fiber optic system $n_1$ = approximately 1.58, and $n_0$ = 1 for air. Using those parameters, an air gap results in R equaling 0.0505, implying that approximately 5% of the light in a fiber is reflected and lost when it tries to cross an air gap. An additional 5% of the light is lost as light enters the glass fiber on the other side of the air gap. This results in a total loss of approximately 10% of the original light in the first optical fiber. However, if the medium between the fibers is water rather than air, $n_0$ is about 1.33 and the total loss becomes about 1.5% of the original. This dramatic reduction in light loss, provides a meaningful illumination difference in the light transmitted to the operative end of handpiece 10. In addition to the foregoing effect, the focusing effect of water is such that less light is lost when transmitted through a water gap than through an air gap.

While the foregoing invention has been described with reference to the specific embodiments thereof, it should be understood by those skilled in the art that various changes can be made and equivalents may be substituted therefore without departing from the true spirit and scope of the invention. All such modifications are intended to be within the claims appended hereto.

What is claimed is:

1. A dental handpiece comprising:
    a housing having a distal end and a proximal end;
    first light conducting means within said housing to conduct light from substantially the proximal end to the distal end of said housing, said first light conducting means having a first terminus adjacent the proximal end of said housing;
    first liquid conducting means within said housing to conduct liquid from substantially the proximal end to the distal end of said housing;
    a connector having a distal end and a proximal end and being adapted for rotational attachment to the proximal end of said housing;
    second light conducting means within said connector to conduct light from the proximal end to the distal end of said connector, said second light conducting means having a second terminus adjacent the distal end of said connector;
    second liquid conducting means within said connector to conduct liquid from the proximal end to the distal end of said connector; and
    a manifold within said housing for sealingly engaging a portion of said connector and said first light conducting means and said first liquid conducting means, said manifold and the distal end of said connector, when said connector is attached to said housing, defining a sealed space through which liquid can flow from said second liquid conducting means to said first liquid conducting means and through which light can be transmitted from the second terminus of said second light conducting means to the first terminus of said first light conducting means.

2. The handpiece of claim 1 wherein said first terminus and said second terminus of said first and second light conducting means, respectively, are located on a central axis of said housing and said connector.

3. The handpiece of claim 1 wherein said connector includes retaining means for engaging a cooperative portion of said housing to retain said connector within said housing.

4. The handpiece of claim 3 wherein said retaining means includes a circular spring clip and said cooperative portion of said housing is a circumferential groove adapted to be engaged by said spring clip.

5. The handpiece of claim 4 wherein said retaining means includes an angular contact ball bearing.

6. The handpiece of claim 5 wherein said spring clip and said bearing occupy substantially the same radial space.

7. The handpiece of claim 1 which includes:
    first air conducting means within said housing to conduct air from substantially the proximal end to the distal end of said housing;
    second air conducting means within said connector to conduct air from the proximal end to substantially the distal end of said connector, said connector and said housing, when said connector is attached to said housing, defining an air pathway through which air can flow from said second air conducting means to said first air conducting means; and
    sealing means for substantially sealing said air pathway from leakage.

8. The handpiece of claim 7 wherein said sealing means includes a seal responsive to pressure in said pathway.

9. The handpiece of claim 8 wherein said sealing means includes a floating O-ring.

10. The handpiece of claim 9 wherein said connector includes said floating O-ring.

11. The handpiece of claim 8 wherein said sealing means further includes the sealing engagement between said manifold and the distal end of said connector.

12. The handpiece of claim 9 wherein said sealing means further includes the sealing engagement between said manifold and the distal end of said connector.

13. The handpiece of claim 10 wherein said sealing means further includes the sealing engagement between said manifold and the distal end of said connector.

* * * * *